(12) United States Patent
Kim et al.

(10) Patent No.: US 12,002,548 B2
(45) Date of Patent: Jun. 4, 2024

(54) METHOD FOR GENOME SEQUENCE ALIGNMENT AND APPARATUS THEREOF

(71) Applicant: ELECTRONICS AND TELECOMMUNICATIONS RESEARCH INSTITUTE, Daejeon (KR)

(72) Inventors: Changdae Kim, Daejeon (KR); Kwang-Won Koh, Daejeon (KR); Kang Ho Kim, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 587 days.

(21) Appl. No.: 17/070,452

(22) Filed: Oct. 14, 2020

(65) Prior Publication Data

US 2021/0287760 A1 Sep. 16, 2021

(30) Foreign Application Priority Data

Mar. 11, 2020 (KR) .................. 10-2020-0029991

(51) Int. Cl.
*G16B 30/10* (2019.01)
(52) U.S. Cl.
CPC .................... *G16B 30/10* (2019.02)
(58) Field of Classification Search
None
See application file for complete search history.

(56) References Cited

U.S. PATENT DOCUMENTS

| 9,323,889 B2 | 4/2016 | Park et al. |
| 9,348,968 B2 | 5/2016 | Park |
| 2014/0100789 A1 | 4/2014 | Choi et al. |
| 2014/0207386 A1 | 7/2014 | Jung et al. |
| 2015/0066384 A1 | 3/2015 | Park |

FOREIGN PATENT DOCUMENTS

| KR | 10-2013-0097440 | 9/2013 |
| KR | 10-2013-0101711 | 9/2013 |
| KR | 10-2015-0026542 | 3/2015 |
| KR | 10-2015-0137373 | 12/2015 |

(Continued)

OTHER PUBLICATIONS

Yongchao Liu and Bertil Schmidt. Long read alignment based on maximal exact match seeds. vol. 28 ECCB 2012, pp. i318-i324 (Year: 2012).*

(Continued)

*Primary Examiner* — Larry D Riggs, II
*Assistant Examiner* — Mary C Leverett
(74) *Attorney, Agent, or Firm* — KILE PARK REED & HOUTTEMAN PLLC

(57) ABSTRACT

An apparatus for genome sequence alignment attempts a search for the hash tables to align a target nucleotide sequence, from a hash table having a large seed size to a hash table having a small seed size, and when there is at least one matched seed to the target nucleotide sequence on a hash table, aligns the target nucleotide sequence by using candidate positions from the hash table without further hash table searching.

6 Claims, 7 Drawing Sheets

Specification includes a Sequence Listing.

(56) References Cited

FOREIGN PATENT DOCUMENTS

| | | | |
|---|---|---|---|
| KR | 10-1584857 | 1/2016 | |
| WO | WO-2018006022 A1 * | 1/2018 | ............. G16B 30/00 |

OTHER PUBLICATIONS

Nauman Ahmed et al. A Comparison of Seed-and-Extend Techniques In Modern DNA Read Alignment Algorithms. 2016 IEEE International Conference on Bioinformatics and Biomedicine (Year: 2016).*

Haowen Zhang et al. Fast and efficient short read mapping based on a succinct hash index. Zhang et al. BMC Bioinformatics (2018) 19:92 (Year: 2018).*

Nicolas Le Scouarnec. Cuckoo++ Hash Tables: High-Performance Hash Tables for Networking Applications. Technicolor Technical Report, Dec. 2017 (Year: 2017).*

Xiao, C. L., Mai, Z. B., Lian, X. L., Zhong, J. Y., Jin, J. J., He, Q. Y., & Zhang, G. (2014). FANSe2: a robust and cost-efficient alignment tool for quantitative next-generation sequencing applications. PloS one, 9(4), e94250. (Year: 2014).*

Ayat Hatem et al., "Benchmarking short sequence mapping tools", BMC Bioinformatics, Jun. 7, 2013, pp. 1-25.

Samuele Girotto et al., Efficient computation of spaced seed hashing with block indexing, BMC Bioinformatics, Nov. 30, 2018, pp. 29-38.

Haowen Zhang et al., "Fast and efficient short read mapping based on a succinct hash index", BMC Bioinformatics, Mar. 9, 2018, pp. 1-14.

Matei Zaharia et al., "Faster and More Accurate Sequence Alignment with SNAP", arXiv:1111.5572v1 [cs.DS] Nov. 23, 2011, pp. 1-10.

* cited by examiner

FIG. 2

Reference genome : ACTGACTGACTGACTGAAAACCCCTTTTGGGG(SEQ ID NO: 1)

Index#1 (Seed Size:8)

| Seed | Location |
| --- | --- |
| ACTGACTG | 0,4,8 |
| CTGACTGA | 1,5,9 |
| TGACTGAC | 2,6 |
| GACTGACT | 3,7 |
| TGACTGAA | 10 |
| GACTGAAA | 11 |
| ACTGAAAA | 12 |
| CTGAAAAC | 13 |
| TGAAAACC | 14 |
| GAAAACCC | 15 |
| AAAACCCC | 16 |
| AAACCCCT | 17 |
| AACCCCTT | 18 |
| ACCCCTTT | 19 |
| CCCCTTTT | 20 |
| CCCTTTTG | 21 |
| CCTTTTGG | 22 |
| CTTTTGGG | 23 |
| TTTTGGGG | 24 |

Index#2 (Seed Size:4)

| Seed | Location |
| --- | --- |
| ACTG | 0,4,8,12 |
| CTGA | 1,5,9,13 |
| TGAC | 2,6,10 |
| GACT | 3,7,11 |
| TGAA | 14 |
| GAAA | 15 |
| AAAA | 16 |
| AAAC | 17 |
| AACC | 18 |
| ACCC | 19 |
| CCCC | 20 |
| CCCT | 21 |
| CCTT | 22 |
| CTTT | 23 |
| TTTT | 24 |
| TTTG | 25 |
| TTGG | 26 |
| TGGG | 27 |
| GGGG | 28 |

Reference genome : ACTGACTGACTGACTGAAAACCCCTTTTGGGG(SEQ ID NO: 1)

Seed:
- ACTGACTG
- CTGACTGA
- TGACTGAC
- GACTGACT
- ACTGACTG
- CTGACTGA
- TGACTGAC
- GACTGACT
- ACTGACTG
- ⋮

FIG. 4

Index#1 (Seed Size:8)

| Seed | Location |
|---|---|
| ACTGACTG | 0,4,8 |
| CTGACTGA | 1,5,9 |
| TGACTGAC | 2,6 |
| GACTGACT | 3,7 |
| TGACTGAA | 10 |
| GACTGAAA | 11 |
| ACTGAAAA | 12 |
| CTGAAAAC | 13 |
| ... | ... |

Index#2 (Seed Size:4)

| Seed | Location |
|---|---|
| ACTG | 0,4,8,12 |
| CTGA | 1,5,9,13 |
| TGAC | 2,6,10 |
| GACT | 3,7,11 |
| TGAA | 14 |
| GAAA | 15 |
| AAAA | 16 |
| AAAC | 17 |
| ... | ... |

Nucleotide sequence : ACTGAAAACCACTTTT(SEQ ID NO: 2)
Threshold value : 4

1. Search on Index#1 (Seed Size : 8)
Candidate#1 : ACTGACTGACTGACTGAAAACCACTTTGGGG → Start : 12, Difference :1
→ The nucleotide sequence is aligned at position 12

SEQUENCE LISTING

<160> NUMBER OF SEQ ID NOS: 3

<210> SEQ ID NO 1
<211> LENGTH: 32
<212> TYPE: DNA
<213> ORGANISM: Artificial Sequence
<220> FEATURE:
<223> OTHER INFORMATION: Synthetic

<400> SEQUENCE: 1
actgactgac tgactgaaaa cccctttttgg gg                32

<210> SEQ ID NO 2
<211> LENGTH: 16
<212> TYPE: DNA
<213> ORGANISM: Artificial Sequence
<220> FEATURE:
<223> OTHER INFORMATION: Synthetic

<400> SEQUENCE: 2
actgaaaacc actttt                                   16

<210> SEQ ID NO 3
<211> LENGTH: 16
<212> TYPE: DNA
<213> ORGANISM: Artificial Sequence
<220> FEATURE:
<223> OTHER INFORMATION: Synthetic

<400> SEQUENCE: 3
actgcaaacc actttt                                   16

METHOD FOR GENOME SEQUENCE ALIGNMENT AND APPARATUS THEREOF

CROSS-REFERENCE TO RELATED APPLICATION

This application claims priority to and the benefit of Korean Patent Application No. 10-2020-0029991 filed in the Korean Intellectual Property Office on Mar. 11, 2020, the entire contents of which are incorporated herein by reference.

BACKGROUND OF THE INVENTION

(a) Field of the Invention

The present invention rerates to a method for genome sequence alignment and an apparatus thereof. More particularly, the present invention relates to a method for genome sequence alignment and an apparatus thereof that are capable of maintaining accuracy while increasing the genome sequence alignment speed using a hash table.

(b) Description of the Related Art

The genome sequence alignment refers to determining where a short nucleotide sequence (base sequence) read from a human or an organism is located in a reference genome composed of a human genome or an entire genome. Since all genomes are different and errors may occur in reading the nucleotide sequence, the position of the nucleotide sequence is determined by searching a position with the most similar nucleotide sequence in the reference genome considering insertion, deletion, and mutation of the nucleotide sequence.

It is very expensive to compose the entire genome of a human or specific species of organism. However, using genome sequence alignment, the entire genome can be composed by only reading a large amount of short nucleotide sequences from humans or organisms, and the entire genome can be analyzed with low cost. Furthermore, through this, it is possible to easily identify the cause of a disease due to a mutation or modification of the gene.

A method for processing genome sequence alignment with a high speed is a genome sequence alignment based on a hash table. This method generates indices (values) of the reference nucleotide sequence in advance by representing reference nucleotide sequences of a reference genome as values of a hash table using a hash function, and enables quick finding the position of the short nucleotide sequence in the reference genome. The unit generating the index of the base sequence is called a seed. The method generates indices using the hash function in the seed unit for all parts of the reference genome, and matches the indices and all parts of the nucleotide sequence to be aligned in the seed unit. At this time, the matching parts are candidates for alignment, and only these candidates are used to calculate the difference between the reference genome and the nucleotide sequence to be aligned. The nucleotide sequence is aligned to the position of the candidate with the largest difference among the calculated differences. However, if the calculated differences are greater than a threshold, alignment fails.

The seed size is an important factor in genome sequence alignment based on the hash table. The index search finds matching positions on the reference genome only when the number of matched bases is larger than the seed size. Thus, as the seed size increases, the index search finds the positions with more matched bases, that is, it finds more similar genes from the reference genome. On the other hand, since it finds the matching positions only when the number of matched bases is large, the probability of genome sequence alignment failing increases. Furthermore, when the seed size is small, the index search finds more candidate positions as the small number of matched bases is considered as a matched position. However, as the number of candidate positions increases, more computation is required to find the most similar position. Thus, sequence alignment time increases.

Recently, as the memory cost of a computer has become cheaper, and a high-density memory product such as a non-volatile memory is launched, it can be a practical genome sequence alignment algorithm if it can gain speed even if more memory space is needed.

SUMMARY OF THE INVENTION

The present invention has been made in an effort to provide a method for genome sequence alignment and an apparatus thereof for maintaining accuracy of the genome sequence alignment while increasing the genome sequence alignment speed using hash tables.

According to an embodiment of the present invention, a method for genome sequence alignment based on hash tables in an apparatus for genome sequence alignment is provided. The method for genome sequence alignment includes: attempting a search for the hash tables to align a target nucleotide, from a hash table having a large seed size to a hash table having small seed size; and when there is at least one matched seed to the target nucleotide sequence on a hash table, aligning the target nucleotide sequence by using candidate positions from the hash table without further hash table searching.

The attempting includes: searching for the hash table having the next seed size to align the target nucleotide sequence when there is no matched seed to the target nucleotide sequence on the hash table having a large seed size.

The aligning the target nucleotide sequence may include: calculating differences by comparing the target nucleotide sequence and the reference genome with respect to each position of the least one matched seed in the reference genome; and aligning the target nucleotide sequence to the position of the seed having the smallest difference among the candidate positions having a difference of less than a threshold.

The method for genome sequence alignment further includes reporting a genetic sequence alignment failure when there is no matched seed to the target nucleotide sequence on the hash table having the smallest seed size.

According to another exemplary embodiment of the present invention, an apparatus for genome sequence alignment based on a hash table is provided. The apparatus for genome sequence alignment includes a memory, a searcher, and an aligner. The memory stores a plurality of hash tables having different seed sizes.

The searcher determines a position on the reference genome to align a target nucleotide sequence by searching a hash table having the largest seed size and searching a hash table having the next seed size when the search in the hash table having the largest seed size has failed for the target nucleotide sequence. The aligner aligns the target nucleotide sequence to the determined position.

The aligner may report a genetic sequence alignment failure when the alignment of the target nucleotide sequence using the hash table with the smallest seed size fails.

The searcher, when there is at least one matched seed to target nucleotide sequence on a hash table, may calculate differences by comparing the target nucleotide sequence and the reference genome with respect to each position of the least one matched seed in the reference genome, and may determine a position of the seed having the smallest difference among positions having a difference of less than a threshold to the position to be align the target nucleotide sequence.

The searcher, when there is no matched seed to target nucleotide sequence on the hash table or no seed having a difference of less than the threshold value, may determine that a search of the hash table has failed.

The searcher, when there is at least one matched seed to target nucleotide sequence on the hash table, may not perform a search in a hash table having the next seed size.

BRIEF DESCRIPTION OF THE DRAWINGS

FIG. 2 is a diagram illustrating hash tables of different sizes according to an embodiment of the present invention.

FIG. 4 is a diagram illustrating an example of a method for genome sequence alignment using hash tables of different seed sizes shown in FIG. 2.

DETAILED DESCRIPTION OF THE EMBODIMENTS

Figure 1:
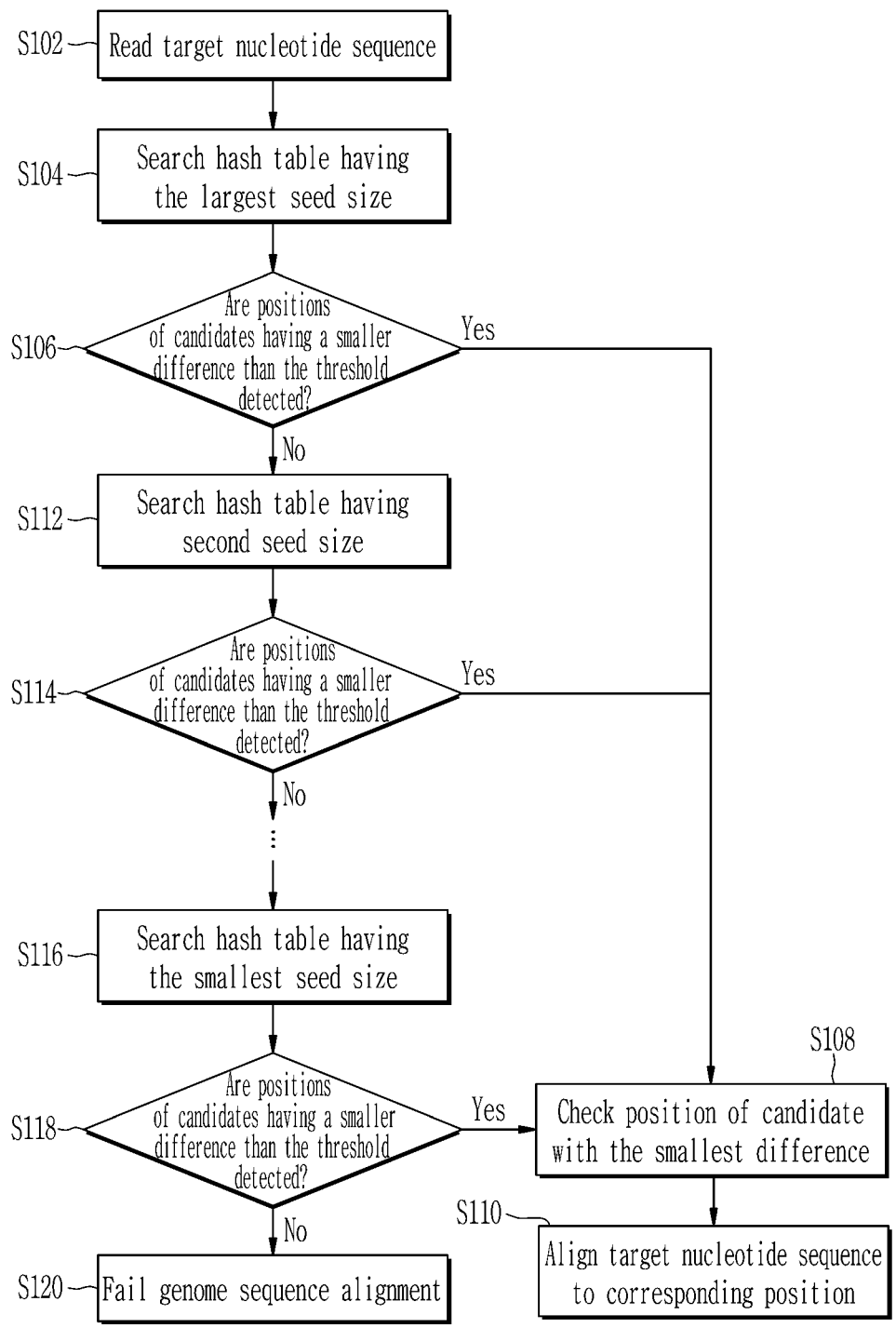
FIG. 1 is a flowchart illustrating a method for genome sequence alignment according to an embodiment of the present invention.

Hereinafter, embodiments of the present invention will be described in detail with reference to the attached drawings so that a person of ordinary skill in the art may easily implement the present invention. The present invention may be modified in various ways, and is not limited thereto. In the drawings, elements that are irrelevant to the description of the present invention are omitted for clarity of explanation, and like reference numerals designate like elements throughout the specification.

Throughout the specification and claims, when a part is referred to "include" a certain element, it means that it may further include other elements rather than exclude other elements, unless specifically indicated otherwise.

Hereinafter, a method for genome sequence alignment and an apparatus thereof according to embodiments of the present invention will be described in detail with reference to the accompanying drawings.

FIG. 1 is a flowchart illustrating a method for genome sequence alignment according to an embodiment of the present invention.

Referring to FIG. 1, the apparatus for genome sequence alignment first reads a target nucleotide sequence to be aligned from the genome sequence (S102).

The apparatus for genome sequence alignment searches the hash table having the largest seed size for the target nucleotide sequence (S104). At this time, the process of searching the hash table is the same as the method of searching the hash table in general genome sequence alignment based on the hash table. The apparatus for genome sequence alignment calculates a hash value using a hash function for each read of the corresponding seed size on the target nucleotide sequence, and checks whether the hash value of each read matches the hash value of the seed corresponding to each entry in the hash table having the largest seed size. Here, the lead represents a fragment of the nucleotide sequence. The apparatus for genome sequence alignment calculates the difference by comparing the target nucleotide sequence with the reference nucleotide sequence of the reference genome indicated by the corresponding entries, when there is a hash value of a seed matching the hash value of at least one read in the hash table with the largest seed size. The apparatus for genome sequence alignment aligns the target nucleotide sequence to be aligned to the position of the reference nucleotide sequence having the smallest difference. However, if the smallest difference is greater than the threshold, it cannot be aligned. In this process, the enhanced speed techniques used in a conventional genome sequence alignment based on the hash table can be applied. The method for searching the hash table will be described in more detail with reference to FIGS. 3 and 4.

As described above, when the apparatus for genome sequence alignment detects the positions of candidates having a smaller difference than the threshold in a hash table having the largest seed size for the reads of the target nucleotide sequence (S106), it checks the position of the candidate with the smallest difference among the differences (S108). Then, the apparatus for genome sequence alignment aligns the target nucleotide sequence to the corresponding position (S110). Then, the genome sequence alignment is terminated.

On the other hand, the apparatus for genome sequence alignment, if there is no candidate with a smaller difference than the threshold in the hash table having the largest seed size for the reads of the target nucleotide sequence (S106), searches in the same way using a hash table with a next seed size, that is, the second seed size (S112).

When the positions of candidates having a smaller difference than the threshold are searched in a hash table having the second seed size for the reads of the target nucleotide sequence (S114), the apparatus for genome sequence alignment aligns the target nucleotide sequence to the position of the candidate with the smallest difference among the differences (S108, S110). Then, genome sequence alignment is terminated.

The apparatus for genome sequence alignment, if there is no candidate with a smaller difference than the threshold in the hash table having the second seed size for the reads of the target nucleotide sequence, searches a hash table with a next seed size.

In this way, the apparatus for genome sequence alignment performs searching by the hash table with the smallest seed size (S116).

The apparatus for genome sequence alignment does not align the target nucleotide sequence unless the positions of candidates having a smaller difference than the threshold are searched in the hash table having the smallest seed size for the reads of the target nucleotide sequence (S118). That is, the genome sequence alignment is failed (S120).

The apparatus for genome sequence alignment reports the genome sequence alignment failure and ends the genome sequence alignment only when the genome sequence alignment is failed even in the hash table having the smallest seed size.

The method for genome sequence alignment according to the embodiment of the present invention has the following differences compared to the conventional genome sequence alignment based on the hash table.

Since the conventional genome sequence alignment uses only one hash table, there is only one seed size. Therefore, if the seed size is large, the alignment often fails, and when the seed size is small, the number of parts to try to align increases, so the alignment speed slows down. On the other hand, the method for genome sequence alignment according to the embodiment of the present invention uses a plurality of hash tables with different seed sizes, and sequentially uses hash tables with a large seed size. Therefore, if the alignment is successful using a hash table with a large seed size, a high alignment speed can be obtained. If the alignment fails using a hash table with a large seed size, the probability of success in aligning is maintained because the hash table with the next seed size is used. In this case, the alignment speed may be slower when the alignment fails in hash tables having a large seed size, but in general genome sequence alignment, since the differences between the target nucleotide sequence to be aligned and the reference genome are often small, the probability of success in aligning does not decrease much even if the seed size is increased to a certain extent. Therefore, using the genome sequence alignment method according to an embodiment of the present invention, it is possible to maintain the probability of alignment success while increasing the genome sequence alignment speed.

Figure 3:
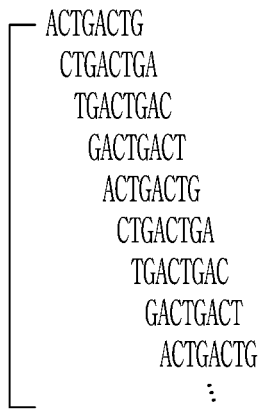
FIG. 3 is a diagram illustrating a method for extracting a seed.

FIG. 2 is a diagram illustrating hash tables of different sizes according to an embodiment of the present invention, and FIG. 3 is a diagram illustrating a method for extracting a seed.

Referring to FIG. 2, an apparatus for genome sequence alignment according to an embodiment of the present invention uses a plurality of hash tables of different seed sizes for genome sequence alignment. When the reference genome is "ACTGACTGACTGACTGAAAACCCCTTTTGGGG (SEQ ID NO:1)" and hash tables with a seed size of 8 and 4 may be formed, the apparatus for genome sequence alignment performs genome sequence alignment using the hash tables with the seed sizes of 8 and 4.

A hash table with a seed size of 8 can be generated as follows.

First, the seeds are extracted by reading the value of the reference nucleotide sequence corresponding to the seed size of 8 while sequentially moving by one base from the first part of the reference genome "ACTGACTGACTGACTGAAAACCCCTTTTGGGG (SEQ ID NO:1)". The extracted seeds are shown in FIG. 3. Generally, DNA nucleotides are represented by letters A, C, G, and T, and each of these letters is referred to as the base.

As shown in FIG. 3, when the seed size is 8, the first seed becomes "ACTGACTG", the second seed becomes "CTGACTGA", and the third seed becomes "TGACTGAC".

In this way, the seeds read from the reference genome are hashed using a hash function to form the hash table with a seed size of 8. At this time, the key of the hash table becomes a hash value generated from the seed, and the value of the hash table may be composed of position information in a reference nucleotide sequence of the seed. The key of the hash table is used as an index.

In the same way, when the seed size is 4, seeds having a seed size of 4 may be extracted from a reference genome, and the extracted seeds may be hashed using the hash function to form the hash table having a seed size of 4. In this case, hash tables having different seed sizes may be distinguished by hash table indexes.

The apparatus for genome sequence alignment according to an embodiment of the present invention performs genome sequence alignment by starting a search from a hash table having a large seed size as the method described in FIG. 1, using two or more hash tables having different seed sizes.

FIG. 4 is a diagram illustrating an example of a method for genome sequence alignment using hash tables of different seed sizes shown in FIG. 2.

Referring to FIG. 4, the apparatus for genome sequence alignment searches a hash table of index #1 with the seed size of 8 for a nucleotide sequence "ACTGAAAACCACTTTT (SEQ ID NO:2)" having a length of 16. The apparatus for genome sequence alignment sequentially reads the nucleotide sequence values corresponding to the length of the seed size of 8 while sequentially moving by one base from first part of the nucleotide sequence "ACTGAAAACCACTTTT (SEQ ID NO:2)" to extract leads.

The apparatus for genome sequence alignment hashes the leads extracted using a hash function, and checks whether there is an entry matching the hashed value in the hash table of index #1 having a seed size of 8. When a seed of the hash value matching the lead "ACTGAAAA" is searched from the hash table of index #1, the apparatus for genome sequence alignment calculates the difference by comparing the nucleotide sequence "ACTGAAAACCACTTTT (SEQ ID NO:2)" with the reference nucleotide sequence corresponding to the position of the seed. At this time, since the calculated difference is 1 and this difference is less than 4 set as a threshold value, the apparatus for genome sequence alignment aligns the nucleotide sequence "ACTGAAAACCACTTTT (SEQ ID NO:2)" to position 12 of the corresponding reference nucleotide sequence.

If the apparatus for genome sequence alignment successfully aligns the nucleotide sequence "ACTGAAAACCACTTTT (SEQ ID NO:2)" using the hash table of index #1 with a seed size of 8, it does not search the hash table of the seed size of 4 and ends genome sequence alignment.

Figure 5:
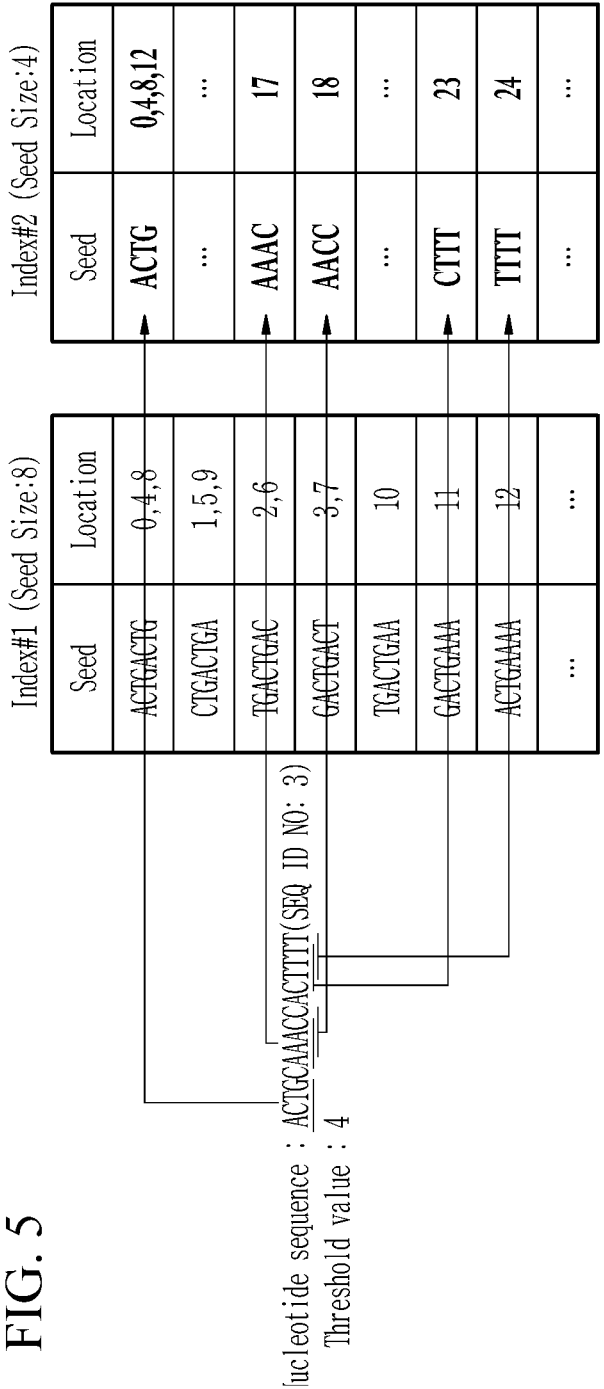
FIG. 5 is a diagram illustrating another example of a method for genome sequence alignment using hash tables of different seed sizes shown in FIG. 2.

FIG. 5 is a diagram illustrating another example of a method for genome sequence alignment using hash tables of different seed sizes shown in FIG. 2. Referring to FIG. 5, the apparatus for genome sequence alignment searches the hash table of index #1 with the seed size of 8 with respect to the nucleotide sequence "ACTGCAAACCACTTTT (SEQ ID NO:3)" having the length of 16. Here, the nucleotide sequence to be aligned "ACTGCAAACCACTTTT (SEQ ID NO:3)" has one more difference with the reference nucleotide sequence compared to the nucleotide sequence "ACTGAAAACCACTTTT (SEQ ID NO:2)" shown in FIG. 4.

The apparatus for genome sequence alignment first searches the hash table of index #1 with the seed size of 8 for the nucleotide sequence "ACTGAAAACCACTTTT (SEQ ID NO:2)". The apparatus for genome sequence alignment sequentially reads the nucleotide sequence values corresponding to the length of the seed size of 8 while sequentially moving by one base from first part of the nucleotide sequence "ACTGCAAACCACTTTT (SEQ ID NO:3)" to extract leads.

The apparatus for genome sequence alignment hashes the leads extracted using a hash function, and checks whether there is an entry matching the hashed value in the hash table of index #1 having a seed size of 8. The apparatus for genome sequence alignment searches the hash table of index #2 with the seed size of 4 corresponding to the next seed size if it is determined that there is no entry matching the hashed value in the hash table of index #1 having a seed size of 8.

The apparatus for genome sequence alignment sequentially reads the nucleotide sequence values corresponding to the length of the seed size of 4 while sequentially moving by one base from first part of the nucleotide sequence "ACTGCAAACCACTTTT (SEQ ID NO:3)" to extract leads.

The apparatus for genome sequence alignment hashes the leads extracted using a hash function, and checks whether there is an entry matching the hashed value in the hash table of index #2 having a seed size of 4. At this time, the matching parts are candidates for alignment, and the apparatus for genome sequence alignment calculates the differences between the reference nucleotide genomes corresponding to only these candidates and the nucleotide sequence to be aligned.

In the case of FIG. 5, since the hash values of the leads of "ACTG", "AAAC", "AACC", "CTTT", and "TTTT" match the key values in the hash table of index #2, the leads of "ACTG", "AAAC", "AACC", "CTTT", and "TTTT" are candidates for alignment. The apparatus for genome sequence alignment attempts alignment with respect to a total of eight candidate positions considering the case where multiple positions are recorded in the entry corresponding to "ACTG" in the hash table of index #2.

The apparatus for genome sequence alignment calculates the differences by comparing the positions between the nucleotide sequence "ACTGCAAACCACTTTT (SEQ ID NO:3)" and the corresponding reference nucleotide sequence with respect to a total of eight candidate positions. At this time, the position on the reference nucleotide sequence having a difference of less than 4 set as the threshold value is 12. Therefore, the nucleotide sequence "ACTGCAAACCACTTTT (SEQ ID NO:3)" is aligned at position 12 on the reference nucleotide sequence.

Meanwhile, referring to the candidates 4-1 to 4-5, in the apparatus for genome sequence alignment, each of the seed positions is position 12 on the reference genome considering the seed positions in the nucleotide sequence "ACTGAAAACCACTTTT (SEQ ID NO:2)". Thus, the apparatus for genome sequence alignment may calculate the differences by comparing the positions between the nucleotide sequence "ACTGCAAACCACTTTT (SEQ ID NO:3)" and the corresponding reference nucleotide sequence with respect to a total of eight candidate positions, but may calculate the differences with respect to the first to third candidates, and one of the 4-1th to 4-5th candidates, that is, a total of four candidate positions. As a result of calculation, the first to third candidates have a difference of greater than the threshold value of 4, and only the 4-1th candidate has a difference of less than the threshold value of 4. Thus, the nucleotide sequence "ACTGCAAACCACTTTT (SEQ ID NO:3)" is aligned to position 12 on the reference genome corresponding to 4-1th candidate 4-1.

Based on FIGS. 4 and 5 described above, in the embodiment of FIG. 4, the difference from the reference genome is calculated for only one position using one entry in the hash table having a seed size of 8, but in the embodiment of FIG. 5, the differences from the reference genome for a total of 4 locations using 5 entries in the hash table having a seed size of 4. FIG. 4 shows an example of fast genome sequence alignment using a hash table having a large seed size, and FIG. 5 shows an example of successful genome sequence alignment using a hash table having a small seed size even if genome sequence alignment fails using a hash table with a large seed size.

That is, when the method for the genome sequence alignment such as an embodiment of the present invention is used, the probability of detecting a position on a reference genome can be maintained while increasing the genome sequence alignment speed.

Figure 6:
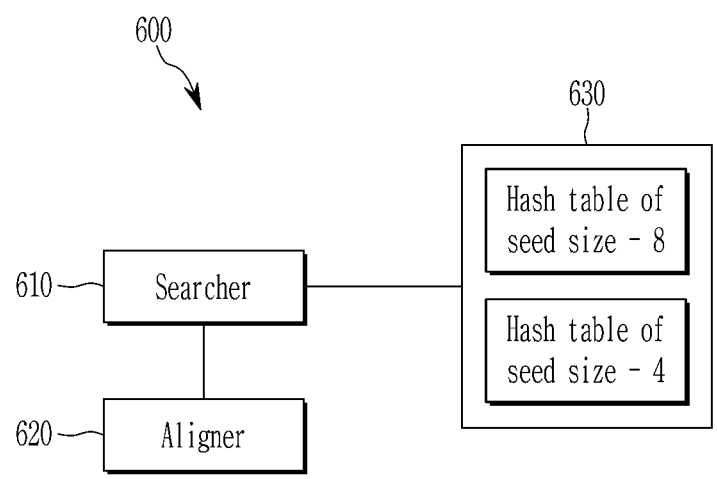
FIG. 6 is a diagram illustrating an apparatus for genome sequence alignment according to an embodiment of the present invention.

FIG. 6 is a diagram illustrating an apparatus for genome sequence alignment according to an embodiment of the present invention.

Referring to FIG. 6, the apparatus 600 for genome sequence alignment includes a searcher 610, an aligner 620, and memory 630.

A plurality of hash tables having different seed sizes are stored in the memory 630, as referred to in FIG. 2. That is, two or more hash tables having different seed sizes may be stored in the memory 630.

The searcher 610 searches the hash table from the largest seed size for the target nucleotide sequence to be aligned. The searcher 610 transmits the position of the candidate having the smallest difference to the aligner 620 when the positions of the candidates having the smaller difference than the threshold are searched as a result of searching the hash table with the largest seed size. Meanwhile, the searcher 610 searches for a hash table with a next seed size if positions of candidates having a smaller difference than a threshold are not searched as the result of searching the hash table at the largest seed size. The searcher 610 searches the hash table in this way, detects a position in the hash table to align the target nucleotide sequence, and then transmits the detected position to the aligner unit 620. On the other hand, if the locations of candidates having a smaller difference than the threshold are not searched even in the hash table having the smallest seed size, the searcher 610 transmits the search failure to the aligner 620.

When the aligner 620 receives the detected position from the searcher 610, it aligns the target nucleotide sequence to the detected position of the reference nucleotide sequence and ends genome sequence alignment. In addition, when the aligner 620 receives the search failure from the searcher 610, it reports a genetic sequence alignment failure, and ends genome sequence alignment.

Figure 7:
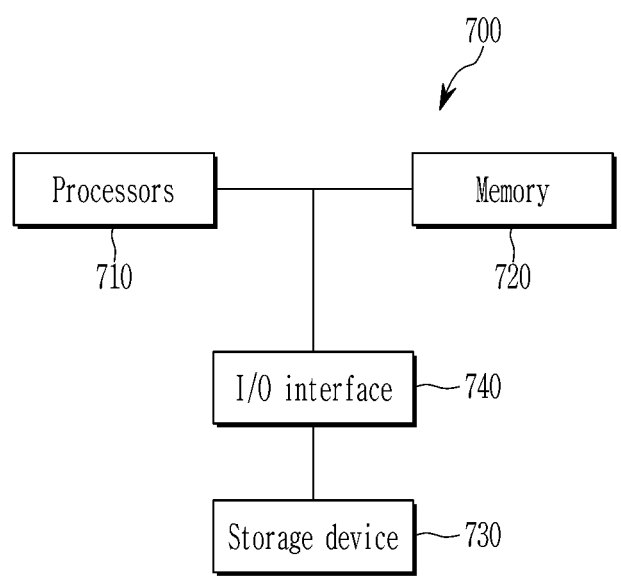
FIG. 7 is a diagram illustrating an apparatus for genome sequence alignment according to another embodiment of the present invention.

FIG. 7 is a diagram illustrating an apparatus for genome sequence alignment according to another embodiment of the present invention, and shows a system that can be used to perform at least some of the functions of the apparatus for genome sequence alignment described with reference to FIGS. 1 to 6.

Referring to FIG. 7, the apparatus 700 for genome sequence alignment includes a processor 710, a memory 720, a storage device 730, and an input/output (I/O) interface 740.

The processor 710 may be implemented as a central processing unit (CPU) or other chipset, a microprocessor, etc.

The memory 720 may be implemented as a medium such as random access memory (RAM), dynamic random access memory (DRAM), rambus DRAM (RDRAM), synchronous DRAM (SDRAM), static RAM (SRAM), etc.

The storage device 730 may be implemented as a hard disk, optical disks such as a compact disk read only memory (CD-ROM), a CD rewritable (CD-RW), a digital video disk ROM (DVD-ROM), a DVD-RAM, a DVD-RW disk, Blu-ray disks, etc., a flash memory, or permanent or volatile storage devices such as various types of RAM.

The I/O interface 740 allows the processor 710 and/or memory 720 to access the storage device 530. In addition, the I/O interface 740 may provide an interface with the outside, for example, the user.

The plurality of processors 710 may perform a function for genome sequence alignment, may load a program command for implementing at least some function of the searcher 610 and the aligner 620 in the memory 720, and may control to perform the operation described with reference to FIGS. 1 to 6. These program commands may be stored in the storage device 730, or may be stored in another system connected through a network.

The embodiment of the present invention stores a plurality of hash tables having different seed sizes in memory and sequentially uses the hash tables from the large seed size for genome sequence alignment, can improve the genome sequence alignment speed when searching in the hash table of a large seed size is successful, and can increase the probability of searching the position to be aligned using the hash table having a small seed size if the search fails in the hash table of the large seed size.

The components described in the example embodiments may be implemented by hardware components including, for example, at least one digital signal processor (DSP), a processor, a controller, an application-specific integrated circuit (ASIC), a programmable logic element, such as an FPGA, other electronic devices, or combinations thereof. At least some of the functions or the processes described in the example embodiments may be implemented by software, and the software may be recorded on a recording medium. The components, the functions, and the processes described in the example embodiments may be implemented by a combination of hardware and software.

The method according to example embodiments may be embodied as a program that is executable by a computer, and may be implemented as various recording media such as a magnetic storage medium, an optical reading medium, and a digital storage medium.

Various techniques described herein may be implemented as digital electronic circuitry, or as computer hardware, firmware, software, or combinations thereof. The techniques may be implemented as a computer program product, i.e., a computer program tangibly embodied in an information carrier, e.g., in a machine-readable storage device (for example, a computer-readable medium) or in a propagated signal for processing by, or to control an operation of a data processing apparatus, e.g., a programmable processor, a computer, or multiple computers. A computer program(s) may be written in any form of a programming language, including compiled or interpreted languages and may be deployed in any form including a stand-alone program or a module, a component, a subroutine, or other units suitable for use in a computing environment. A computer program may be deployed to be executed on one computer or on multiple computers at one site or distributed across multiple sites and interconnected by a communication network.

Processors suitable for execution of a computer program include, by way of example, both general and special purpose microprocessors, and any one or more processors of any kind of digital computer. Generally, a processor will receive instructions and data from a read-only memory or a random access memory or both. Elements of a computer may include at least one processor to execute instructions and one or more memory devices to store instructions and data. Generally, a computer will also include or be coupled to receive data from, transfer data to, or perform both on one or more mass storage devices to store data, e.g., magnetic, magneto-optical disks, or optical disks. Examples of information carriers suitable for embodying computer program instructions and data include semiconductor memory devices, for example, magnetic media such as a hard disk, a floppy disk, and a magnetic tape, optical media such as a compact disk read only memory (CD-ROM), a digital video disk (DVD), etc. and magneto-optical media such as a floptical disk, and a read only memory (ROM), a random access memory (RAM), a flash memory, an erasable programmable ROM (EPROM), and an electrically erasable programmable ROM (EEPROM) and any other known computer readable medium. A processor and a memory may be supplemented by, or integrated into, a special purpose logic circuit.

The processor may run an operating system (08) and one or more software applications that run on the OS. The processor device also may access, store, manipulate, process, and create data in response to execution of the software. For purpose of simplicity, the description of a processor device is used as singular; however, one skilled in the art will be appreciated that a processor device may include multiple processing elements and/or multiple types of processing elements. For example, a processor device may include multiple processors or a processor and a controller. In addition, different processing configurations are possible, such as parallel processors.

Also, non-transitory computer-readable media may be any available media that may be accessed by a computer, and may include both computer storage media and transmission media.

The present specification includes details of a number of specific implements, but it should be understood that the details do not limit any invention or what is claimable in the specification but rather describe features of the specific example embodiment. Features described in the specification in the context of individual example embodiments may be implemented as a combination in a single example embodiment. In contrast, various features described in the specification in the context of a single example embodiment may be implemented in multiple example embodiments individually or in an appropriate sub-combination. Furthermore, the features may operate in a specific combination and may be initially described as claimed in the combination, but one or more features may be excluded from the claimed combination in some cases, and the claimed combination may be changed into a sub-combination or a modification of a sub-combination.

Similarly, even though operations are described in a specific order on the drawings, it should not be understood as the operations needing to be performed in the specific order or in sequence to obtain desired results or as all the operations needing to be performed. In a specific case, multitasking and parallel processing may be advantageous. In addition, it should not be understood as requiring a separation of various apparatus components in the above described example embodiments in all example embodiments, and it should be understood that the above described program components and apparatuses may be incorporated into a single software product or may be packaged in multiple software products.

It should be understood that the example embodiments disclosed herein are merely illustrative and are not intended to limit the scope of the invention. It will be apparent to one of ordinary skill in the art that various modifications of the example embodiments may be made without departing from the spirit and scope of the claims and their equivalents.

What is claimed is:

1. A computer-implemented method for genome sequence alignment based on hash tables in an apparatus for genome sequence alignment, the method comprising:
generating a plurality of hash tables of different seed sizes, wherein generating the plurality of hash tables comprises:
extracting seeds of a first seed size from a reference nucleotide sequence,
generating a hash table of the first seed size by calculating a hash value of each seed among the extracted seeds of the first seed size using a hash function,
extracting seeds of a second seed size from the reference nucleotide sequence,
generating a hash table of the second seed size by calculating a hash value of each seed among the extracted seeds of the second seed size using the hash function,
generating reads of the first seed size of a target nucleotide sequence;
calculating a hash value of each read among the reads of the first seed size using the hash function;
determining the success or failure of the genetic sequence alignment of the target nucleotide sequence using the hash table of the first seed size, by comparing the hash value of each read and a hash value of each seed in the hash table of the first seed size;
when the genetic sequence alignment of the target nucleotide sequence using the hash table of the first seed size has failed, generating reads of the second seed size of a target nucleotide sequence, wherein the second seed size is smaller than the first seed size;
calculating a hash value of each read among the reads of the second seed size using the hash function;
determining the success or failure of the genetic sequence alignment of the target nucleotide sequence using the hash table of the second seed size, by comparing the hash value of each read among the reads of the second seed size and a hash value of each seed in the hash table of the second seed size; and
controlling the apparatus for genome sequence alignment to enable terminating of generating reads of the target nucleotide sequence and calculating hash values of reads, based on the determining of the success or failure of the genetic sequence alignment.

2. The method of claim 1, wherein the determining the success or failure of the genetic sequence alignment of the target nucleotide sequence using the hash table of the first seed size includes:
checking whether the hash value of each read matches a hash value of each seed in a hash table of the first seed size;
determining a location of the matched seed as candidate position;
calculating differences by comparing the target nucleotide sequence and the reference genome with respect to each candidate position; and
determining a position of the seed having the smallest difference among the candidate positions having a difference of less than a threshold as a position to be aligned to the target nucleotide sequence.

3. The method of claim 1, further comprising reporting a genetic sequence alignment failure when there is no matched seed to the target nucleotide sequence on the hash table having the smallest seed size.

4. An apparatus for genome sequence alignment based on hash tables, the apparatus comprising:
  a processor; and
  a memory that stores instructions and a plurality of hash tables having different seed sizes, wherein the instructions when executed by the processor, cause the apparatus to:
  generating a plurality of hash tables of different seed sizes by:
    extracting seeds of a first seed size from a reference nucleotide sequence,
    generating a hash table of the first seed size by calculating a hash value of each seed among the extracted seeds of the first seed size using a hash function,
    extracting seeds of a second seed size from the reference nucleotide sequence, and
    generating a hash table of the second seed size by calculating a hash value of each seed among the extracted seeds of the second seed size using the hash function,
  generate reads of the first seed size of a target nucleotide sequence;
  calculate a hash value of each read among the reads of the first seed size using the hash function;
  determine the success or failure of the genetic sequence alignment of the target nucleotide sequence using the hash table of the first seed size, by comparing the hash value of each read and a hash value of each seed in the hash table of the first seed size;
  when the genetic sequence alignment of the target nucleotide sequence using the hash table of the first seed size has failed, generate reads of the second seed size of a target nucleotide sequence, wherein the second seed size is smaller than the first seed size;
  calculate a hash value of each read among the reads of the second seed size using the hash function;
  determine the success or failure of the genetic sequence alignment of the target nucleotide sequence using the hash table of the second seed size, by comparing the hash value of each read among the reads of the second seed size and a hash value of each seed in the hash table of the second seed size; and
  enable terminating of generating reads of the target nucleotide sequence and calculating hash values of reads, based on the determining of the success or failure of the genetic sequence alignment.

5. The apparatus of claim 4, wherein the instructions when executed by the processor, further cause the apparatus to: report a genetic sequence alignment failure when the genetic sequence alignment of the target nucleotide sequence using the hash table with the smallest seed size fails.

6. The apparatus of claim 4, wherein when determine the success or failure of the genetic sequence alignment of the target nucleotide sequence using the hash table of the first seed size, the instructions when executed by the processor, further cause the apparatus to: check whether the hash value of each read matches a hash value of each seed in a hash table of the first seed size, determine a location of the matched seed as candidate position, calculate differences by comparing the target nucleotide sequence and the reference genome with respect to each candidate position, and determine a position of the seed having the smallest difference among the candidate positions having a difference of less than a threshold as a position to be aligned to the target nucleotide sequence.

* * * * *